United States Patent [19]

Aldridge

[11] 4,276,060
[45] Jun. 30, 1981

[54] CHROMATOGRAPHIC HYDROGEN ISOTOPE SEPARATION

[75] Inventor: Frederick T. Aldridge, Livermore, Calif.

[73] Assignee: The United States of America as represented by the United States Department of Energy, Washington, D.C.

[21] Appl. No.: 41,364

[22] Filed: May 22, 1979

[51] Int. Cl.³ .............................................. B01D 15/08
[52] U.S. Cl. .......................................... 55/67; 55/68; 55/386; 176/37
[58] Field of Search ............. 210/31 C, 198 C; 55/67, 55/68, 386, 74, 75; 252/301.1, 466 R; 176/37

[56] References Cited

U.S. PATENT DOCUMENTS

| | | | |
|---|---|---|---|
| 3,156,548 | 11/1964 | Perry | 55/386 X |
| 3,220,164 | 11/1965 | Golay | 55/67 |
| 3,237,380 | 3/1966 | Barrett | 55/67 |
| 3,309,844 | 3/1967 | Hemstreet et al. | 55/75 |
| 3,793,435 | 2/1974 | Reilly et al. | 55/74 X |
| 3,883,346 | 5/1975 | Martin | 75/0.5 BA |
| 3,891,413 | 6/1975 | Sievers | 210/31 C |
| 3,937,649 | 2/1976 | Ridgell | 55/68 X |
| 3,940,912 | 3/1976 | Buchner | 55/16 |
| 4,096,639 | 6/1978 | Sandrock | 34/15 |
| 4,096,641 | 6/1978 | Sandrock | 34/15 |
| 4,159,966 | 7/1979 | Roberts | 55/386 X |

OTHER PUBLICATIONS

Chromatography by Heftmann Reinhold Pub. Co., N.Y., pp. 656–659, 1961.
Gas Chromatographic Separations of Hydrogen Isotopes by Glueckauf in Proceedings of the Symposium on Isotope Separation, Amsterdam 1957, Ch. 15, pp. 210–225.

Primary Examiner—John Adee
Attorney, Agent, or Firm—William S. Bernheim; Roger S. Gaither; James E. Denny

[57] ABSTRACT

Intermetallic compounds with the $CaCu_5$ type of crystal structure, particularly $LaNiCo_4$ and $CaNi_5$, exhibit high separation factors and fast equilibrium times and therefore are useful for packing a chromatographic hydrogen isotope separation colum. The addition of an inert metal to dilute the hydride improves performance of the column. A large scale mutli-stage chromatographic separation process run as a secondary process off a hydrogen feedstream from an industrial plant which uses large volumes of hydrogen can produce large quantities of heavy water at an effective cost for use in heavy water reactors.

25 Claims, 7 Drawing Figures

CHROMATOGRAPHIC HYDROGEN ISOTOPE SEPARATION

BACKGROUND OF THE INVENTION

The invention described herein was made at Lawrence Livermore Laboratory in the course of or under contract W-7405-ENG-48 for the U.S. Department of Energy and the University of California.

The invention relates to hydrogen isotope separation and, more particularly, to chromatographic separation of hydrogen isotopes using intermetallic compounds which form hydrides.

At a time when traditional energy resources are in increasingly short supply, nuclear reactors are a major potential source of energy which has already been highly developed. Heavy water moderated reactors provide many advantages, including permitting operation with natural uranium or thorium, but the cost and availability of the necessary heavy water supply are significant factors in plant economics and severe obstacles to widespread use. The United States, at present, does not have the capability to produce commercial amounts of heavy water in sufficient quantities for large scale deployment of heavy water moderated reactors.

Heavy water has been separated from natural water by using the differences in physical and chemical properties of the different isotopic species. Large scale production of heavy water has been performed by electrolysis, distillation, chemical exchange, and dual temperature exchange. Common to these methods is a high cost and/or a low efficiency. A modern plant in Canada, using a hydrogen sulfide dual temperature exchange technique, can produce 800 tons/yr; one year's production is the amount required for one moderate sized power reactor. Production costs are presently in the range of $160/Kg.

Chromatography is a chemical separation method having many variations. In general, chromatography is a method by which substances originally in a mixture are separated from each other by the selective process of distribution between two heterogeneous phases. The distribution occurs dynamically between a mobile phase and a stationary phase. There are four heterogeneous phase combinations, one of which is a gas-solid system in which the sample interacts with a solid by the process of adsorption. The components of a mixture, which have different solubilities in the stationary phase, separate by migrating at different rates.

Intermetallic compounds are materials composed of two or more types of metal atoms. They are homogeneous, composite substances and differ in structure from the constituent metals. Some intermetallic compounds react with hydrogen to form binary and ternary hydrides. The hydrogen atom density in some of these hydrides, such as $LaNi_5H_6$, is very high. Certain of these hydrides can serve as a means for hydrogen storage if the reaction between hydrogen and intermetallic compound is fast, reversible, and occurs at convenient temperatures and pressures. Steward et al., "Storage of Hydrogen Isotopes in Intermetallic Compounds," Lawrence Livermore Laboratory, UCRL-77455 (April 1976), describe the use of hydrides for hydrogen storage. Particular emphasis is placed in the Steward et al article on the family of compounds of the formula $AB_5$ where A is a lanthanide and B is a transition metal, usually nickel, cobalt, or iron. U.S. Pat. No. 3,883,346 describes a nickel-lanthanum alloy for hydrogen storage, while U.S. Pat. Nos. 4,096,639 and 4,096,641 disclose nickel-calcium alloys for hydrogen storage.

Deuterium has been separated experimentally from hydrogen using displacement chromatography in a chromatographic column packed with palladium. Such a separation is described by Glueckauf and Kitt, Proceedings of the First International Symposium on Isotope Separation, Amsterdam 1957, Ch. 15, Interscience, New York, 1958. The separation is based on the characteristic that palladium absorbs hydrogen more strongly than deuterium. Because of this difference in absorption, as a mixture of hydrogen and deuterium passes through a palladium packed column, the deuterium is concentrated in front of the hydrogen. With natural hydrogen, which contains a very small fraction of deuterium, complete separation will not occur, but the deuterium will be concentrated in the front few percent of the hydrogen as it emerges from the column. However, the high cost of palladium precludes its use in a large scale commercial process.

It is the object of the invention to provide a method for improved heavy water production on a large scale.

It is another object of the invention to provide intermetallic compounds with a high separation factor.

It is a further object of the invention to produce a chromatographic hydrogen separation column with a high enrichment factor.

It is another object of the invention to provide an economically viable deuterium separation process that can be run as a secondary process off a hydrogen feedstream from a conventional industrial plant which uses large volumes of hydrogen.

SUMMARY OF THE INVENTION

The invention includes improved methods and apparatus for chromatographic separation of hydrogen isotopes, the use of certain hydride-forming intermetallic compounds in chromatographic hydrogen isotope separation columns, and a large-scale multi-stage chromatographic process designed to be run as a secondary process off a hydrogen feedstream from a conventional plant. The compounds belong to the general class of alloys with a $CaCu_5$ type of crystal structure. One preferred class includes $LaNi_{(5-x)}Co_x$ compounds, of which $LaNiCo_4$ has the highest separation factor. Another preferred class includes $LaNi_5$-type compounds in which the La is replaced by Ca. $CaNi_5$ has a separation factor similar to $LaNiCo_4$. $CaNi_{(5-x)}Cu_x$ compounds are also advantageous.

The method of operating a chromatographic column is improved by diluting the intermetallic alloy, or any other hydride forming metal filling the column, by adding an inert metal power. The use of an inert metal in the column is also part of the invention.

BRIEF DESCRIPTION OF THE DRAWINGS

The invention and its further objects and advantages will be better understood from the following detailed description of various embodiments, cited for the sake of illustration with reference to the accompanying drawings, in which.

DETAILED DESCRIPTION OF PREFERRED EMBODIMENTS

The intermetallic-hydride chromatographic-separation process uses the property of certain intermetallic compounds and other metals of reacting reversibly with hydrogen to form solid metal hydrides. Natural hydrogen contains one part in six thousand of deuterium. A group of compounds of the general formula $AB_5$, where A is a rare earth metal or calcium and B is iron, nickel, cobalt, or copper, can absorb up to six hydrogen atoms per atom of intermetallic compound. Thus the hydrogen atom density in these hydrides is very high. $LaNi_5$ appears to be the best of these compounds for hydrogen storage.

Most of the deuterium analogs of these metal hydrides are thermodynamically less stable and, therefore, exhibit higher hydrogen (deuterium) vapor pressure at any specified temperature. If this difference is large enough and the equilibrium between hydrogen gas and hydride is sufficiently rapid, a chromatographic column filled with hydride-forming metal can be used to separate the deuterium from a protium-deuterium mixture. The separation factor can be used as one measure of the suitability of a hydride for use in isotope separation. The separation factor is defined as the isotopic abundance of deuterium in hydrogen gas divided by the isotopic abundance of deuterium in the metal hydride which is in equilibrium with the gas. For isotope separation it is desired that this separation factor exceed one by as much as possible.

The invention includes the use of various intermetallic compounds which display a $CaCu_5$-crystalline type structure for chromatographic hydrogen isotope separation.

The compound $LaNi_5$ has been found to be an excellent hydrogen storage material and, therefore, is useful for the chromatographic separation process. This compound absorbs hydrogen reversibly in a few minutes at two or three atmospheres pressure. It absorbs hydrogen more strongly than deuterium. It is not poisoned by gases such as oxygen, carbon monoxide, carbon dioxide, or water vapor and, consequently, can be used with industrial hydrogen sources which frequently contain these gases.

Figure 1:
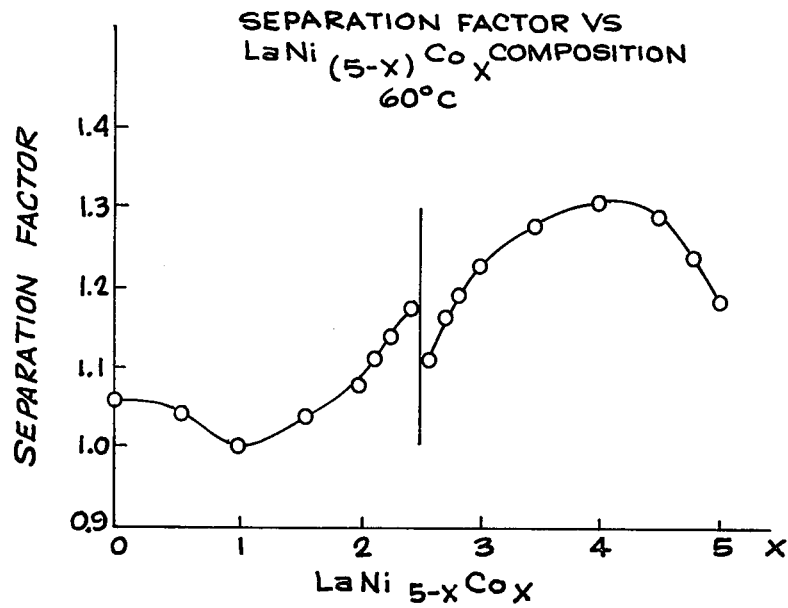
FIG. 1 shows the separation factor of $LaNi_{(5-x)}Co_x$ compounds.

Other $LaNi_5$-type alloys can also be used, in particular, the class of lanthanum-nickel-cobalt compounds of the formula $LaNi_{(5-x)}Co_x, 0 \leq x \leq 1$. A plot of the separation factors of these compounds is shown in FIG. 1. The compound $LaNiCo_4$ has the highest separation factor, 1.3, plus a fast equilibrium time and a favorable equilibrium pressure curve.

To the extent lanthanum compounds can be replaced by calcium compounds the process is less costly. $CaNi_5$ shows a separation factor of 1.15, and reaches equilibrium faster and has a flatter equilibrium pressure curve than $LaNiCo_4$. $CaNi_{(5-x)}Cu_x$ alloys are also useful for chromatographic separation, and have separation factors near 1.3.

The separative properties of these $AB_5$ compounds can be improved by adding small amounts of other elements, such as aluminum, magnesium, chlorine or sodium, to the alloys in order to change the separation factor, equilibrium pressure or equilibrium speed.

The chromatographic column includes a long metal tube packed with the desired hydride-forming alloy in powdered form. The packed column is one of the basic types of separation columns used in gas chromatography. A packed column is a tube filled with a sorption material, usually in granular or powdered form, through which the carrier gas flows. Analytical packed columns typically have 1–5 m length and 1–8 mm inside diameter. Much wider columns are used for preparative-scale separation.

The intermetallic alloy in the separation column can be diluted with an inert metal powder, such as copper, nickel, or iron in order to limit temperature changes due to the heat of hydriding. The invention includes an improved separation column packed with both a hydride forming metal and an inert (non-hydride forming) metal, and the use of inert metals with any metal hydride in a hydrogen isotope separation column. The preferred ratio is approximately four parts inert metal to one part hydride.

In the displacement chromatographic separation process, the metal-filled column is initially loaded with a relatively inert gas, such as argon. The deuterium-protium gas mixture is then flowed into one end of the column, forcing the inert gas out the other end. As the isotopically mixed hydrogen stream enters the column, it flows through hydride already saturated with hydrogen, isotopically exchanging with it to some extent, until it reaches unsaturated metal, where it reacts to create the hydride. As the hydrogen flows down the column, it isotopically equilibrates with the hydride and becomes enriched in deuterium, while the hydride becomes deuterium-depleted, since the deuterium prefers the gas phase more than protium does. When this deuterium-hydrogen reacts, it forms an enriched hydride, which further enriches the gas passing over it. Thus, the deuterium fraction in the injected hydrogen stream is continuously concentrated at the boundary between hydrogen and the inert gas, as the boundary reaches the bottom of an optimally operated column, essentially all the deuterium will be in the first few percent of the hydrogen gas which comes off the column. This type of chromatography differs from the usual mode of gas chromatography in that a carrier gas is not used.

The invention further includes a large scale chromatographic hydrogen isotope separation plant which processes the hydrogen feedstream from a conventional main plant. To be suitable for a large scale industrial process the intermetallic hydrides require high protium-deuterium separation factors, fast equilibrium rates between the solid and gaseous phases, and relatively low operating temperatures so that the hydrogen can be desorbed before repeating the separation cycle. The rare-earth transition metal compounds, particularly alloys with the $CaCu_5$ crystal structure, and more particularly $LaNiCo_4$ and $CaNi_4Cu$, have the requisite properties for use in a plant economically operating as part of another plant which has a large internal flow of molecular hydrogen. The separation columns could be operated in an ammonia plant or oil refinery. The hydrogen is internally diverted to remove its deuterium and then returned.

In order to extract essentially all the deuterium in the feedstream, the column is only partially filled with isotopically mixed supply hydrogen, and then filled the rest of the way with previously isotopically depleted hydrogen. The column fraction F to be filled with supply hydrogen is approximately $F=(K-1)/K$ where K is the separation factor.

The operation of the deuterium separation cycle of an individual column is shown in FIGS. 2 A–E. In the first step, shown in FIG. 2A, the column 10, packed with a suitable intermetallic compound, is first filled with argon 13 at 250 psi from tank 12 through inlet pipe 14 while valves 16, 18, 20, 22, and 24 are closed.

Figure 2A:
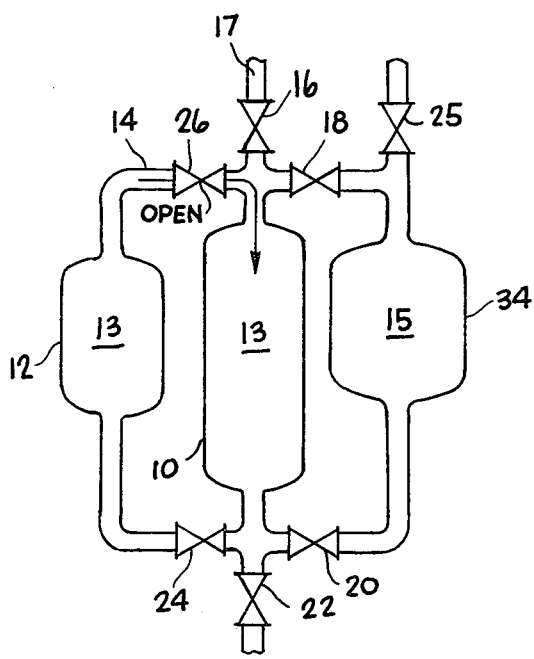
FIGS. 2 A–E show the deuterium separation cycle of a chromatographic column.
Figure 2B:
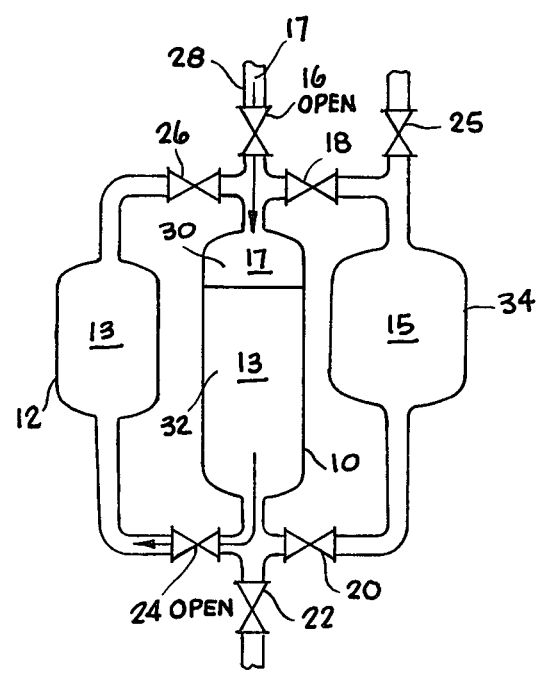

In the second step, shown in FIG. 2B, valve 26 is closed and valve 16 is opened so that the top fraction F of the column 10, is filled with new hydrogen 17, i.e., isotopically mixed hydrogen, through inlet pipe 28 from a hydrogen surge tank (not shown) to which a hydrogen feedstream from a main plant has been diverted. Thus a zone 30 filled with a supply of hydrogen 17 of column 10 forms hydride and isotopically selectively equilibrates with the hydride, while a zone 32 remains filled with argon 13.

Figure 2C:
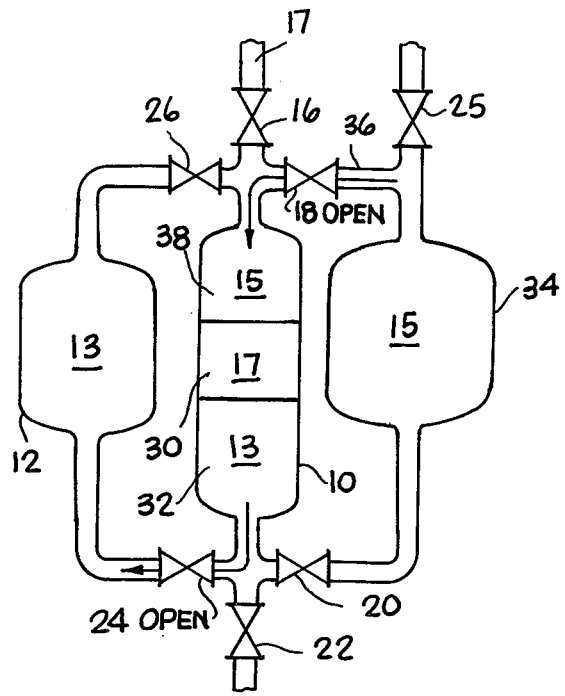

In the next step, shown in FIG. 2C, the supply hydrogen 17 is pushed through the column by depleted hydrogen 15. The valve 16 is closed and valve 18 is opened, allowing the depleted hydrogen 15 to flow from tank 34 through inlet pipe 36 to form zone 38 of depleted hydrogen 15 behind the zone 30 of supply hydrogen 17 which is bounded at the front by zone 32 of argon 13. As the zone 30 flows down the column 10 it isotopically equilibrates with the hydride formed and the front of zone 30 becomes enriched in deuterium while the remainder of zone 30 becomes depleted in deuterium.

Figure 2D:
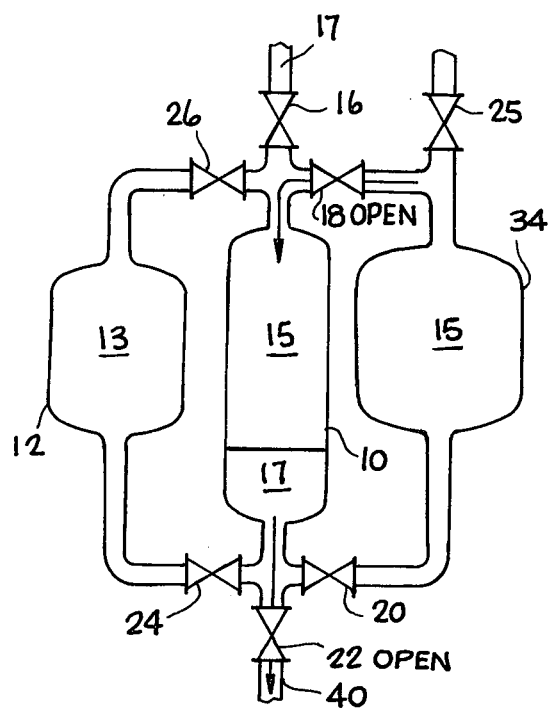
Figure 2E:
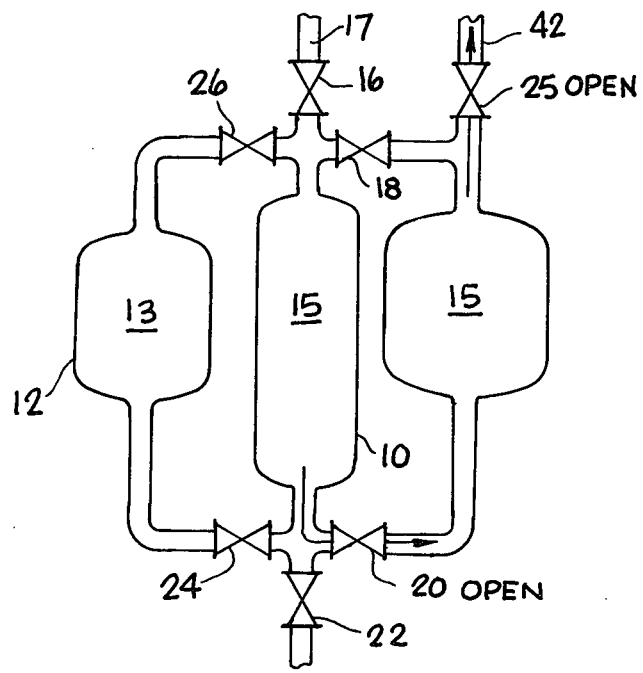

In the fourth step, shown in FIG. 2D, the enriched front of zone 30 has reached the bottom of column 10, the valve 24 is closed and valve 22 is opened so that the enriched hydrogen is pushed out through outlet pipe 40. In the final step, shown in FIG. 2E, valve 22 is closed, valve 20 is opened, and column 10 is pumped out. Part of the depleted hydrogen 15 is saved for the next cycle, while the rest if returned through valve 25 through return pipe 42 to the feedstream for the main plant. After the column 10 is pumped out, the cycle is repeated.

Figure 3:
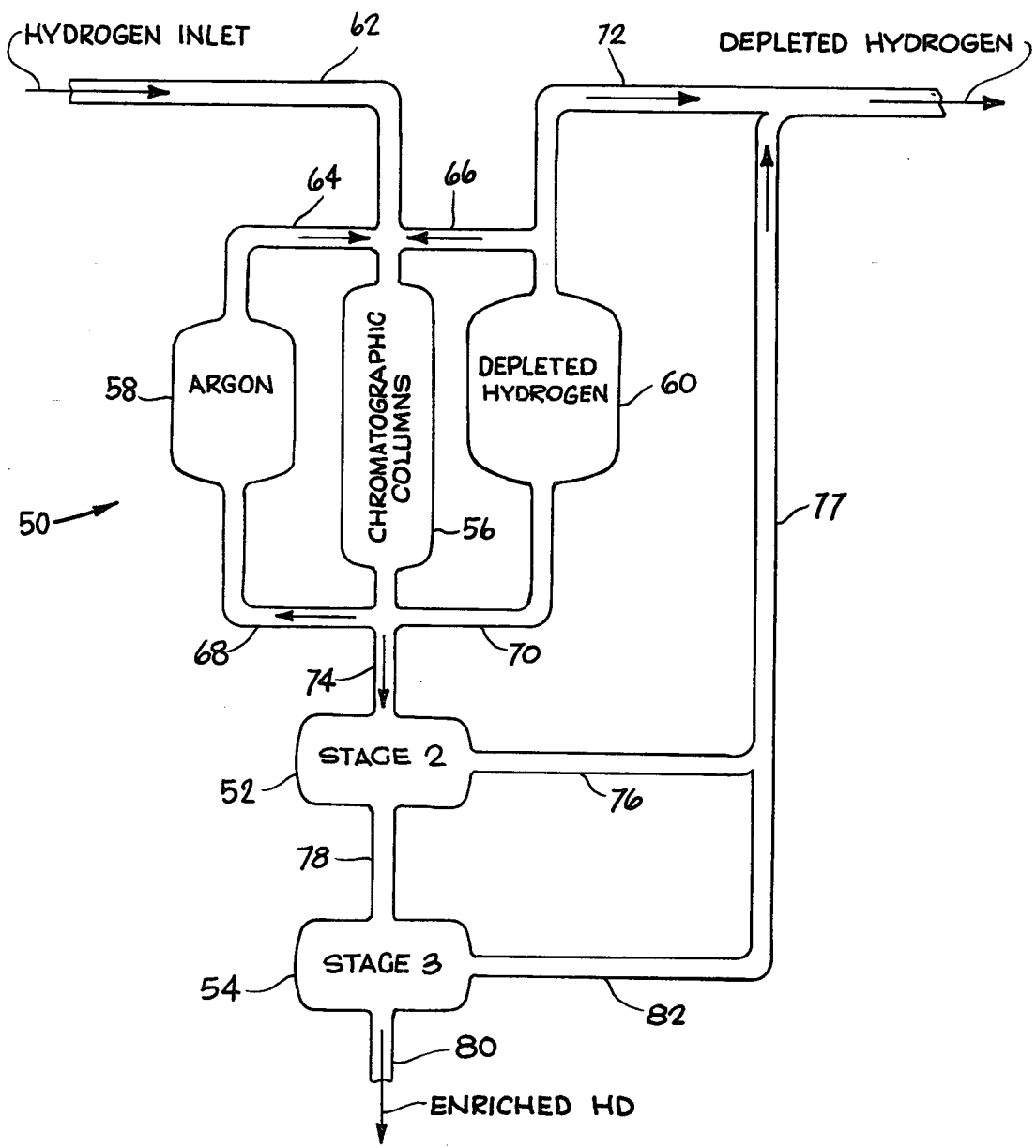
FIG. 3 shows a diagram of a three-stage 100 ton/yr heavy water plant run in conjunction with a conventional ammonia production plant.

A preferred embodiment of a chromatographic deuterium separation process, shown schematically in FIG. 3, has been designed to run off a 1025 ton/day ammonia plant and produce 100 ton/yr of heavy water. The plant has three stages, designated 50, 52 and 54. The first stage 50 comprises column 56, argon tank 58, and depleted hydrogen tank 60. The supply hydrogen is inlet through pipe 62 at a rate of 45,000 ft$^3$/min. The supply hydrogen contains 0.03% HD. Argon is inlet through pipe 64 at 5,000 ft$^3$/min and depleted hydrogen through pipe 66 at 117,000 ft$^3$/min. The operation of this stage (and the other two stages) is the cycle described above and shown in FIGS. 2 A–E. The argon returns to tank 58 through pipe 68 at 5,000 ft$^3$/min and the depleted hydrogen returns to tank 60 through pipe 70 at 157,500 ft$^3$/min. The depleted hydrogen is returned to the main plant feedstream through pipe 72 at 40,500 ft$^3$/min.

The enriched hydrogen from first stage 50, containing 0.3% HD, passes through pipe 74 to second stage 52 at 4,500 ft$^3$/min. Depleted hydrogen is returned through pipe 76 at 4,050 ft$^3$min. The second stage 52 operates according to the above described cycle and enriched hydrogen, containing 3% HD, passes through pipe 78 at 450 ft$^3$/min to the third stage 54. From the third stage, enriched hydrogen, containing 30% HD, passes through outlet pipe 80 at 45 ft$^3$/min while depleted hydrogen returns through pipe 82 at 405 ft$^3$/min to the feedstream.

This embodiment uses an intermetallic compound with a separation factor of 1.4, an enrichment factor of 10 per stage, a column pressure of 250 psia, a column operating temperature near ambient, and a 15-minute column or process cycle time. The column must be small in at least one dimension to dissipate the heat of hydriding on absorption and to absorb heat from the surroundings on desorption. The column is therefore, preferably, a bundle of narrow diameter tubes immersed in an appropriate heat transfer liquid with some of the tube absorbing hydrogen while others desorb, so the net heat flow from the bundle is zero.

EXAMPLES

The following are examples of intermetallic compounds that have been prepared in the laboratory, and the measured separation or enrichment factors:

(1) The intermetallic compound LaNiCo$_4$ was prepared by mixing together 1.59 g La, 0.67 g Ni, and 2.70 g cobalt and arc melting the mixture on a water cooled copper block under an argon atmosphere.

The resulting ingot was annealed at 1000° Centigrade for 24 hours. The compound was then saturated with hydrogen at a temperature of 60° Centigrade and pressure of 500 PSIA to form a compound of approximate composition LaNiCo$_4$H$_{4.3}$.

This compound had a separation factor for deuterium-hydrogen isotope separation of 1.31.

(2) The intermetallic compound CaNi$_4$Cu was prepared by mixing 1.22 g Ca, 5.52 g Ni and 1.49 g Cu and then melting and annealing the mixture as in example 1, except than an annealing temperature of 850° Centigrade was used. The amount of calcium used was more than required for the composition CaNi$_4$Cu to allow for losses which occur during the melting. The compound was saturated with hydrogen at 60° Centigrade and 500 PSIA pressure to form the compound CaNi$_4$CuH$_{5.1}$.

This compound had a separation factor for deuterium-hydrogen isotope separation of 1.32.

(3) 79 g of LaNiCo$_4$ powder was mixed with 402 g of nickel powder. The mixture was packed into a brass tube of 90 inch length and ¼ inch diameter. The tube was pressurized to 400 PSI with argon. Hydrogen gas was allowed to flow into one end of the tube at a rate of 110 standard pressure cubic centimeters per minute, pushing the argon out the other end. When all of the argon was displaced from the column, hydrogen gas began flowing from the other end of the column.

The first hydrogen to flow out of the column was found to be enriched in deuterium by a factor of 3.6.

Of course, other embodiments and adaptations may be provided without going beyond the scope of the invention. It will be obvious to those skilled in the art that various changes may be made without departing from the scope of the invention and the invention is not to be considered to be limited to what is described in the specification.

What we claim is:

1. A method of chromatographically separating hydrogen isotopes in a separation column comprising passing isotopically mixed hydrogen gas through a separation medium comprising a hydride forming intermetallic alloy selected from the group of intermetallic alloys with a CaCu$_5$ type of crystal structure.

2. The method of claim 1 wherein the alloy is selected from the group of alloys with the formula $LaNi_xCo_{(5-x)}$.

3. The method of claim 2 wherein the alloy is $LaNiCo_4$.

4. The method of claim 1 wherein the alloy is selected from the group of alloys with the formula $CaNi_xCu_{(5-x)}$.

5. The method of claim 4 wherein the alloy is $CaNi_4Cu$.

6. The method of claim 1 including the addition of small amounts of other elements selected from the group aluminum, magnesium, chlorine, and sodium.

7. A composition packed in a chromatographic hydrogen isotope separation column comprising:
   a hydride forming intermetallic compound in powdered form, selected from the group of alloys with the $CaCu_5$ type of crystal structure; and
   an inert metal in powdered form which dilutes the hydride forming intermetallic compound to improve the performance of the separation column.

8. The composition of claim 7 wherein the ratio of inert metal to metal hydride is approximately 4 to 1.

9. The composition of claim 7 wherein the intermetallic compound is selected from the group of alloys with the formula $LaNi_xCo_{(5-x)}$.

10. The composition of claim 9 wherein the intermetallic compound is $LaNiCo_4$.

11. The composition of claim 7 wherein the intermetallic compound is selected from the group of alloys with the formula $CaNi_xCu_{(5-x)}$.

12. The composition of claim 11 wherein the intermetallic compound is $CaNi_4Cu$.

13. An improved method for chromatographic hydrogen isotope separation comprising:
    packing a chromatographic separation column with hydride forming intermetallic alloys in powdered form selected from the group of alloys with $CaCu_5$ type of crystal structure; and
    flowing isotopically mixed hydrogen gas through the column to separate the isotopes by displacement chromatography.

14. The method of claim 13 wherein the intermetallic alloy is diluted in the column with an inert metal powder.

15. The method of claim 13 wherein the intermetallic alloy is selected from the group of alloys with the formula $LaNi_xCo_{(5-x)}$.

16. The method of claim 15 wherein the intermetallic alloy is $LaNiCo_4$.

17. The method of claim 13 wherein the intermetallic alloy is selected from the group of alloys with the formula $CaNi_xCu_{(5-x)}$.

18. The method of claim 17 wherein the intermetallic alloy is $CaNi_4Cu$.

19. An improved method for separating hydrogen isotopes chromatographcially, comprising:
    packing a separation column with a mixture of a hydride forming metal in powdered form and an inert metal powder to dilute the hydride forming metal; and
    flowing isotopically mixed hydrogen gas through the column to separate the hydrogen isotopes by displacement chromatography.

20. The method of claim 19 wherein the ratio of inert metal to hydride forming metal is approximately 4 to 1.

21. A multi-stage plant for the enrichment of heavy hydrogen isotopes in a stream of isotopically mixed hydrogen from a main plant, comprising;
    a staged series of chromatographic hydrogen isotope separation columns, each column packed with an intermetallic alloy selected from the group of alloys with $CaCu_5$ type of crystal structure diluted with inert metal powder, the output of each stage being input into the next stage, a stream of isotopically mixed hydrogen being input into the first column and making a single pass through the series of columns, thereby resulting in higher enrichment factors at each successive stage; and
    a hydrogen return pipe from each column for returning isotopically depleted hydrogen to the main plant.

22. The plant of claim 21 wherein the intermetallic alloy is selected from the group of alloys with the formula $LaNi_xCo_{(5-x)}$.

23. The plant of claim 22 wherein the alloy is $LaNiCo_4$.

24. The plant of claim 21 wherein the intermetallic alloy is selected from the group of alloys with the formula $CaNi_xCu_{(5-x)}$.

25. The plant of claim 24 wherein the alloy is $CaNi_4Cu$.

* * * * *